(12) United States Patent
Selby et al.

(10) Patent No.: US 9,055,879 B2
(45) Date of Patent: Jun. 16, 2015

(54) DEVICE AND METHOD FOR ASSEMBLING AN ELECTRONIC DEVICE AND A FLEXIBLE ELEMENT FOR FACILITATING ASSEMBLY OF ELECTRONIC COMPONENTS

(71) Applicant: SUUNTO OY, Vantaa (FI)

(72) Inventors: Tapio Selby, Vantaa (FI); Ossi Lehtinen, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 25 days.

(21) Appl. No.: 13/917,668

(22) Filed: Jun. 14, 2013

(65) Prior Publication Data

US 2014/0371568 A1   Dec. 18, 2014

(30) Foreign Application Priority Data

Jun. 14, 2013 (FI) ...................................... 20135650

(51) Int. Cl.
| | |
|---|---|
| *H01R 13/11* | (2006.01) |
| *A61B 5/0416* | (2006.01) |
| *A61B 5/02* | (2006.01) |
| *H01R 12/58* | (2011.01) |
| *H01R 12/70* | (2011.01) |
| *H01R 12/79* | (2011.01) |
| *H05K 7/14* | (2006.01) |
| *A61B 5/0492* | (2006.01) |

(Continued)

(52) U.S. Cl.
CPC ................. *A61B 5/0416* (2013.01); *A61B 5/02* (2013.01); *H01R 12/58* (2013.01); *H01R 12/7029* (2013.01); *H01R 12/79* (2013.01); *H05K 7/14* (2013.01); *A61B 5/0492* (2013.01); *A61B 5/6804* (2013.01); *H01R 12/712* (2013.01); *H01R 13/17* (2013.01); *H01R 43/205* (2013.01); *A61B 2562/125* (2013.01); *Y10T 29/49218* (2015.01); *H01R 13/11* (2013.01)

(58) Field of Classification Search
USPC ........... 439/137, 281, 37, 729, 725, 890, 567; 411/480; 600/385, 386
See application file for complete search history.

(56) References Cited

U.S. PATENT DOCUMENTS

| | | |
|---|---|---|
| 3,750,094 A | 7/1973 | Zenkich |
| 4,490,005 A | 12/1984 | Hovey |

(Continued)

FOREIGN PATENT DOCUMENTS

| | | |
|---|---|---|
| GB | 1486865 | 9/1977 |
| GB | 2425181 | 10/2006 |
| WO | WO2009020274 A1 | 2/2009 |

*Primary Examiner* — Alexander Gilman
(74) *Attorney, Agent, or Firm* — Terence P. O'Brien (57) ABSTRACT

The invention concerns an electronic device, method for assembling components of an electronic device and a flexible cap for facilitating assembly of an electronic component of an electronic device. The electronic device has a housing and at least one male connection portion for providing a detachable connection of the electronic device to a female snap, and where the male connection portion comprises an elongate stud. An end portion of said stud is adapted to receive a flexible cap of a conductive sheet material having a top surface to fit on the top of the stud and at least two side elements, The side elements are formed as legs joined to the top surface by a first bend of the sheet material and are aligned generally along the wall of the end portion of the stud. An electrical connection and a mechanical lock between the end portion and the printed circuit board is created by flexible deformation of the side members when sliding the cap and the end portion through an aperture in the printed circuit board.

21 Claims, 8 Drawing Sheets

(51) Int. Cl.
*A61B 5/00* (2006.01)
*H01R 12/71* (2011.01)
*H01R 13/17* (2006.01)
*H01R 43/20* (2006.01)

(56) References Cited

U.S. PATENT DOCUMENTS

| | | | | |
|---|---|---|---|---|
| 5,401,188 A | * | 3/1995 | Kosmala | 439/567 |
| 5,419,713 A | * | 5/1995 | Northey | 439/567 |
| 5,509,814 A | * | 4/1996 | Mosquera | 439/82 |
| 5,592,719 A | * | 1/1997 | Eto et al. | 24/453 |
| 5,645,063 A | | 7/1997 | Straka, Jr. | |
| 5,921,811 A | * | 7/1999 | Hsu | 439/567 |
| 5,947,769 A | * | 9/1999 | Leonard et al. | 439/607.53 |
| 6,042,420 A | * | 3/2000 | Long | 439/570 |
| 6,230,392 B1 | * | 5/2001 | Clark et al. | 29/739 |
| 6,966,795 B2 | * | 11/2005 | Xu | 439/571 |
| 7,182,610 B2 | * | 2/2007 | Lin | 439/79 |
| 8,814,574 B2 | | 8/2014 | Selby et al. | |
| 2007/0285868 A1 | | 12/2007 | Lindberg et al. | |
| 2013/0131484 A1 | | 5/2013 | Pernu et al. | |

* cited by examiner

DEVICE AND METHOD FOR ASSEMBLING AN ELECTRONIC DEVICE AND A FLEXIBLE ELEMENT FOR FACILITATING ASSEMBLY OF ELECTRONIC COMPONENTS

RELATED APPLICATIONS

The present application claims priority to Finnish Patent Application Serial No. 20135650 filed on Jun. 14, 2013. The present application corresponds to co-pending U.K. Patent Application No. 1310635.6.

FIELD OF INVENTION

The present invention relates to connectors in devices relating to health, sports and other personal equipment. More specifically, the present invention relates to connectors conveying electrode and other low-voltage signals with high reliability requirements in a potentially harsh environment and while being subject to considerable mechanical stress. Such connectors are used for example in heart rate and electromyograph monitors for connecting a usually male connection portion detachably to a female snap in a belt or garment.

BACKGROUND OF THE INVENTION

Currently, there are heart rate monitor belts which people can wear underneath their clothing in order to monitor their heart rate. Such belts are typically designed such that a telemetric transmitter is detachably connected to a belt having two electrodes which are in contact with the user's skin in the chest region of the user's torso. The electrodes identify an electric ECG pulse caused by the heart and then the detachable telemetric transmitter transmits data indicative of the user's heart beat with the use of wireless magnetic near field communication or a radio signal to a remote receiver provided with a display. In many instances the remote receiver is provided in the form of a wrist watch, wrist top computer or other similar display carried by a user, typically on the user's wrist.

Similarly, the fusion between wearable and ubiquitous computing and outdoor activities like sports, produce equipment with various sensors and electrodes attached to or placed on different parts of the body. The usually passive electrodes and the sensor unit they feed with signals need to be interconnected, and both components need to be detachable for replacement or service.

Since various acceleration and magnetic sensors can be integrated in small and lightweight devices, the telemetric data to be transferred may, instead of or in addition to the heart rate, comprise a plurality of measured variable data, such as working frequency, pedaling rate and pedaling frequency, travel speed, etc. The data to be transferred may additionally comprise data required for the identification of the user and/or the transmitter device.

U.S. application Ser. No. 11/808,391 filed Jun. 8, 2007 and published as US 2007/0285868 which is herein incorporated by reference in its entirety, for instance, discloses a heart rate monitor belt which comprises a plurality of electrodes and a detachable telemetric transmitter.

It is preferably to have a telemetric transmitter or sensor unit which is detachable. From a consumer point of view, a user is typically sweating while using a sports device like a heart rate monitor belt and it is therefore advantageous to be able to separate the electronic device from the belt, shoe or garment that is carrying it, so that the carrier can be washed. From a manufacturing point of view, the process for manufacturing the carrier is substantially different from that of manufacturing a transceiver or sensor unit, and therefore it is beneficial to be able to manufacture the components separately. Additionally, it is usually beneficial if the electronic devices are interchangeable between a plurality of carriers.

Though there are several alternative methods for connecting especially a telemetric transmitter to a heart rate monitor belt containing the necessary electrodes, the industry has almost entirely adopted the use of a pair of standard garment snaps. These standard garment snaps typically are mounted on the material of a heart rate monitor belt and virtually their entire thickness of around 4 mm protrudes from the outer surface of the belt. In principle, snaps provide a convenient way with almost guaranteed user acceptance to both mechanically fix devices in place, and to provide an electrical connection between them.

Due to shortcomings in size and reliability of existing "snap" technology and other methods for detachably connecting health monitoring and sports devices to electrodes, it has not been realistic to incorporate electrodes directly in garments. The primary road block to such incorporation has been the size and bulkiness of the standard garment snaps. No clothing manufacture, nor consumer, has wanted 4 mm protrusions from their garments such as tops, shirts and sports bras.

Therefore, the garment industry has incurred a long felt need for an improved method of detachably connecting a health monitoring or sports device to an article of clothing which does not compromise the integrity and utility of the underlying garment. However, especially the telemetric devices manufacturing industry has adopted certain standards which relate to the use of a pair of male studs on a telemetric transmitter to be detachably snapped in to a pair of snaps on a heart rate monitor belt. As such, it would not be economical to wholly redesign the male portions of telemetric transmitters and the method in which they connect to an object having the necessary electrodes for measuring a user's heart rate.

Thus, there exists a need for a snap which fulfils the requirements of the garment industry but which fits in with the design and production methods of the manufacturing industry. Several critical issues arise when attempting to merely minimize the existing standardized snap. The main issue is the integrity of the connection between the male stud and the snap. Any movement of the male stud within the snap will create electrical noise which makes it difficult if not impossible to accurately measure parameters such as a user's heart beat. Additionally, as a user is typically involved in strenuous activity while utilizing the product, the connection needs to withstand and support the attached device during such activity. As the size and depth of a snap decreases, the more critical becomes the mechanical design of it to withstand the forces, and to ensure a reliably and stable electrical connection under all circumstances becomes a very delicate design problem indeed.

Further yet, users typically sweat while undergoing strenuous activity wearing the product. As a reliable electrical connection is necessary between the sensor device and the connected electrodes on the user's skin, it is important to keep the connection moisture free to reduce the likelihood of any shorts. Similarly, the problem is compounded for users who wish to utilize a heart rate monitor under water, for example while swimming or diving.

Therefore, there exist numerous challenges in the art to the development of a means of detachably connecting e.g. a telemetric transmitter to a garment having electrodes for monitoring a user's heart beat which aims to satisfy user's need, the garment manufacturer's needs and the needs of health and sport goods manufacturers.

Partially the problem has been solved in the co-pending U.S. patent application Ser. No. 13/832,736 by the same applicant, the entire content of which is included herein by reference. In the solution presented, the snap size and thickness has been significantly reduced, and the electrical connection between a male connection portion and a socket region of a snap has been improved. Currently, the standard snap thickness in the industry is around or above 4 mm. With the design of the snap presented in U.S. patent application Ser. No. 13/832,736, the maximum thickness of the snap can be between 1 to 3 mm. Thus, utilizing such a design the overall size of the snap can be reduced by 50-70% or more. This reduction in size enables one to integrate health and sport device electrodes into garments in an acceptable manner.

However, the male portion of a snap has two ends, one being connected to the PCB of the health or sports device, like a telemetric heart rate monitor transmitter, the other end protruding from the device as a stud to be snapped into a socket connected to an electrode. The above mentioned solution addresses the design of the stud end and how it interconnects with the socket. However, also the end of the male portion connected to the PCB (Printed Circuit Board) of the device is subject to the same forces and circumstances as the other end. The problem of securing the fastening and electrical connection between the male portion of the snap and the PCB has previously been solved by providing threads to screw the male portion of the snap into place, by welding it to the plastic case of the device with ultrasound, etc. However, these measures are a solution for the mechanical fastening of the male part, and are directed to the mid-portion of it. The end to be fitted to the PCB has so far been conventionally designed, providing gold plating and a friction-based electrical connection. Also, in order to account for variations in the manufacturing process, an electrical wire may be soldered between the male portion of the snap and the PCB, or spring contacts may be used to improve the connection between the male portion and the PCB. Standard PCB spring contacts are however complicated in construction and require separate assembly, like any other components on the PCB.

During the circumstances and for reasons that have been explained above, there is a need for an improved and simplified connection device. The quality of the electrical connection to the PCB is of course as important as in the other end and is, despite a fairly reliable mechanical fastening, subject to small movements and manufacturing tolerances causing noise. Also, only a minimum amount of wear at the contact surface caused by such movement drastically reduces the signal quality.

SUMMARY OF THE INVENTION

It is an object of the present invention to provide an electronic device having an improved connection capability to a female snap provided by an inventive male portion of the snap.

It is an important aspect of the present invention to provide an electronic device having a housing and at least one male connection portion for providing a detachable connection of the electronic device to a female snap, said male connection portion comprising an elongate stud. The stud or male snap member has the following parts and features:

a male head portion capable of fitting within a socket region of a snap, said male head portion forming a first terminal end of the elongated stud, an end portion opposite said male head portion forming a second terminal end of the elongated stud and providing an electrical connection from said electronic device in said housing to said female snap, a mid-portion between the male head portion and the end portion at which said stud is fastened to said housing, said at least one end portion is extending from a first side of a printed circuit board of said electronic device through an aperture in said board.

According to the invention, in the inventive device the end portion is adapted to receive a flexible cap of a conductive sheet material, the cap has a top surface to fit on the top of said second terminal end and at least two side elements, which are formed as legs joined to the top surface by a first bend of the sheet material. The side elements are generally aligned along the wall of said end portion, to create an electrical connection and a mechanical lock between the end portion and the printed circuit board by flexible deformation of the side members when sliding the cap and the end portion through the aperture.

The advantages of such a structure are diverse:

A continuous spring force is obtained in the electrical contact, without breaks or noise. The mechanical lock provided by the cap also serves as a mechanical installation fixture of the male snap member to the PCB. No screws or any separate fastening operations are necessary. The cap is inexpensive to manufacture, and can be used on all kinds of devices where there is a need to connect a stud-like member to a printed circuit board. In a telemetric heart rate transmitter 2 studs are usually enough, connecting the transmitter to 2 ECG electrodes. In an EMG (electromyograph) device, any number of connectors, distributed over the body in a decentralized manner, may be needed to detect the weak EMG signals from muscles or tissues that are intended to be monitored.

The inventive design also automatically correctly aligns the PCB in the housing, as the male snap members fastened to the housing will go through the apertures in the PCB and create a spring force at each aperture when sliding through the apertures. The same spring forces also offer a suitable tolerance for small dimensional errors that may occur in the parts. The inventive design can be made very flat and is space-saving also on the PCB board due to the simplicity of the construction.

According to specific embodiments of the invention, the side elements of the flexible cap may have anchor members formed by a second bend opposite the first bend and in a transverse direction with respect to the direction of the side elements. The anchor members may be directed outwards from the side elements to engage with the edge of said aperture of the printed circuit board, or they may be directed inwards from the side elements to engage with the wall of the end portion, or both.

In some embodiments the surface of the side element is formed as a plane, in other embodiments the surface of the side element may be curved with respect to the direction of the normal of the top surface. The side elements may also have an area between the first and the second bend that is bent or corrugated, in order to add friction and spring forces between the flexible cap and the aperture.

The inventive device may be a telemetric pulse transmitter to be attached to ECG electrodes in an electrode belt with a snap connection, a telemetric pulse transmitter to be attached to ECG electrodes integrated in a garment with a snap connection, or an electromyograph to be attached to EMG electrodes integrated in a garment with a snap connection, just to mention a few examples.

The invention is also directed to a method for assembling components of an electronic device having a printed circuit board and at least one male snap connection portion for providing a detachable connection between said electronic device and a female snap. The inventive method comprises the steps of:

providing said at least one male connection portion as an elongate stud with a male head portion forming a first terminal end of the elongated stud, an end portion opposite the male head portion forming a second terminal end of the elongated stud, and a mid-portion between the male head portion and the end portion at which the stud is fastened a housing of said device, providing at least one flexible cap of a conductive sheet material, the cap having a top surface to fit on the top of the second terminal end of the male connection portion, at least two side elements each formed as a leg joined to the top surface by a first bend of the sheet material, the side elements being aligned along the wall of said end portion, providing the printed circuit board with at least one aperture aligned and adapted to receive said flexible cap and the second terminal end of the male connection portion;

providing a flexible cap in a position between the second terminal end of each male connection portion and the aperture of the printed circuit board;

connecting the printed circuit board with the male connection portion and cap by sliding the flexible cap and the second terminal end into the aperture of the printed circuit board to form an electrical connection and a mechanical lock between the end portion and the printed circuit board by flexible deformation of the side members.

Embodiments of the inventive method include providing the flexible cap with an anchor member formed by a second bend opposite the first bend in a general direction outwards with respect to the direction of the side elements, whereby the flexible cap is inserted into the aperture first, whereafter the second terminal end is slid into the flexible cap to form a connection between the printed circuit board and the male connection portion.

According to an alternative embodiment, the flexible cap is first slid onto the second terminal end, whereafter the second terminal end is slid into the aperture to form a connection between the printed circuit board and the male connection portion.

Furthermore, the invention concerns a flexible cap for facilitating assembly of an electronic component of an electronic device, said component having at least one elongated stud-like connecting member with a first male snap connection portion providing a detachable connection between said male and a female snap, and a second and opposite end portion forming a second terminal end said stud and providing an electrical connection between an electronic device to the female snap. The inventive cap is made of a conductive sheet material and having a generally horizontal top surface, at least two generally vertical side elements each of which is formed as a leg joined to the top surface by a first bend of said sheet material, whereby the cap is adapted to create an electrical connection and a mechanical lock between said electronic component and an aperture of a printed circuit board of said electronic device on the other hand, by flexible deformation of said side members when said connecting member is slid into said cap and passed through said aperture of said printed circuit board.

The side elements of the flexible cap may have an anchor member formed by a second bend opposite the first bend of the side elements in a transverse direction with respect to the direction of the side elements, whereby the anchor member may be directed outwards from the side elements to engage with the edge of said aperture on the side of its insertion direction of said printed circuit board, or inwards from the side elements to engage with the wall of said end portion, or both.

The surface of the side element may be formed as a plane or it may be curved with respect to the direction of the normal of said top surface. The cap is preferably made out of one piece of a stainless steel sheet and comprises three side elements.

BRIEF DESCRIPTION OF THE DRAWINGS

FIG. 4 a-f shows a variety of examples of the flexible element on which the present invention is based;

FIG. 7 a-c shows enlarged details of the inventive assembly embodiments.

DETAILED DESCRIPTION OF EXEMPLARY EMBODIMENTS

Figure 1:
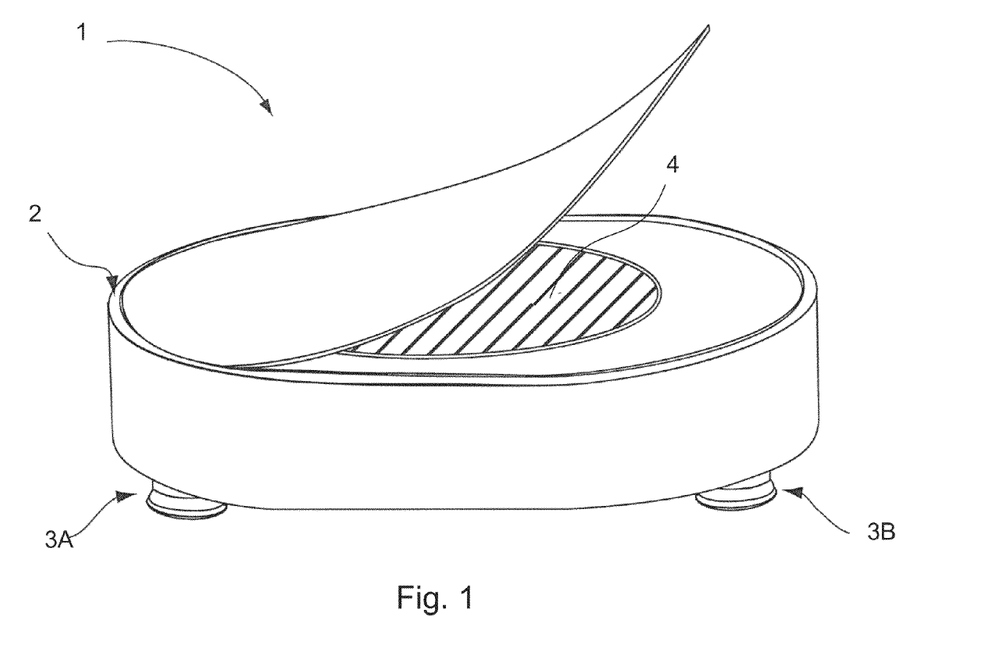
FIG. 1 shows a generic body of a typical telemetric device comprising male snap ends in accordance with an embodiment of the present invention.
Figure 2:
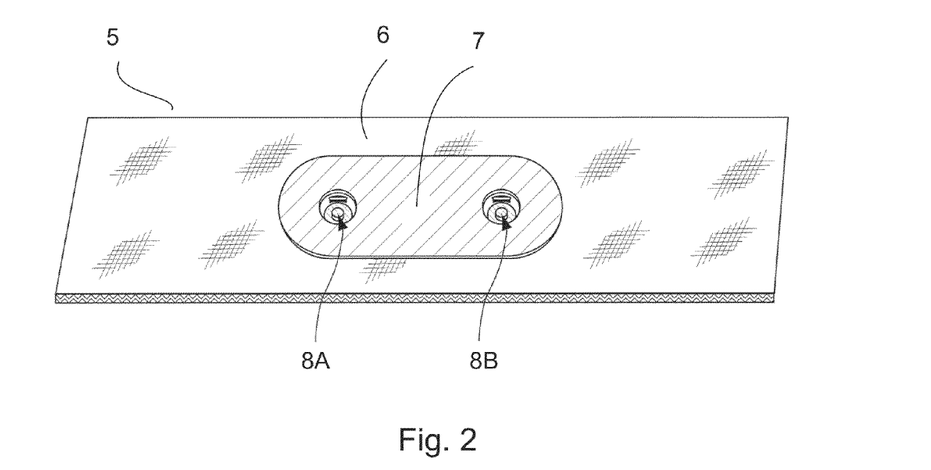
FIG. 2 shows an example of a garment or heart rate monitor belt having two snap sockets corresponding to the male ends shown in FIG. 1.

An example of a telemetric device 1 which is compatible with the garment 6 shown in FIG. 2. The telemetric device 1 has a body portion 2, an aperture 4 for housing for example a battery, a surface surrounding the aperture 4 surrounded by an outer lip 2a and a cover 3, which can be for example a flexible sticker type cover with or without a graphic or textual display. Additionally, the telemetric device has two studs 5 having an exposed male end for being detachably coupled to the snaps 8A and 8 of garment 6.

FIG. 2 shows an example of a garment or belt 6 which has a top material layer 7 and two electrodes (not shown) which can be coupled to the back of garment 6 or to another subsequent material layer. Each electrode is connected to a snap, 8A and 8B. In a typical arrangement, the electrode attached to each snap would extend in a direction away from the other snap. As such, there will be an area between the two snaps which may or may not include an electrode or similar material.

Figure 3:
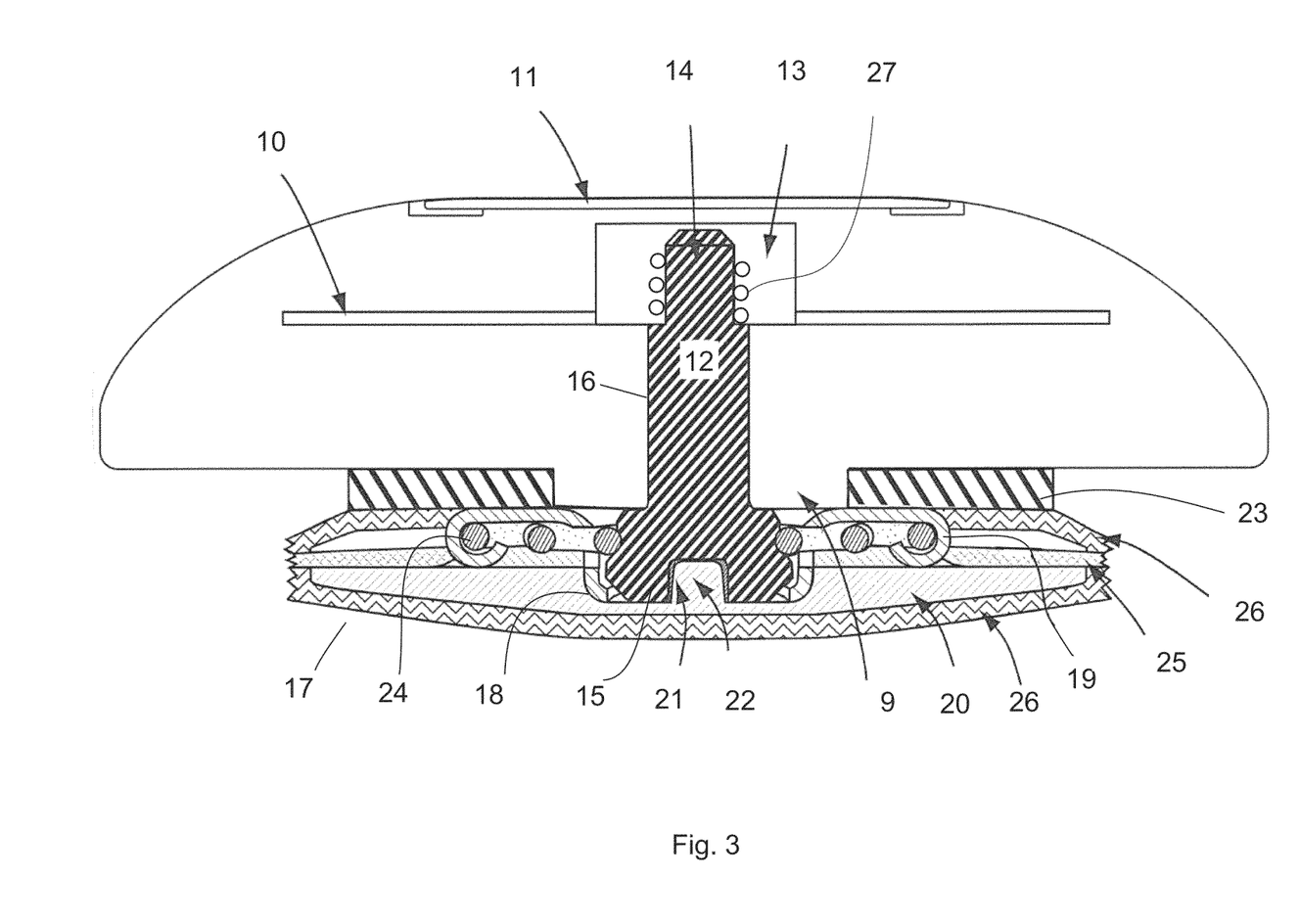
FIG. 3 shows a cutaway of a telemetric transceiver having a stud and male end inserted within the socket region of a snap, the construction forming a basis which to improve upon for the present invention.

FIG. 3 shows in cross-section a complete snap assembly according to a prior solution by the present applicant. An electronic device 9, for example a telemetric heart rate transmitter 9 is shown having a PCB 10 holding the electronics of the device (not shown), a cover 11 for accessing e.g. a battery compartment of the device, a stud 12 forming the male portion of the snap assembly, and connector 13 connecting the end portion 14 of the stud 12 to the PCB 10.

The end portion 14 of the stud is opposite the male head portion 15, which fits into the receiving socket 18 of the snap 17. The end portion 14 extends from a mid-portion 16 of the stud. The division between the mid-portion and the end portion may be an imaginary break, or there may be a change in diameter, as shown. The mid-portion 16 may have a threaded portion (not shown) which facilitates the fastening to the body of the device 9 by screwing.

The terminal end of the end portion 14 can be chamfered inwards e.g. to facilitate easier assembly and safer electromechanical connection between the stud 12 and the PCB 10 of the device 9. The connector 13 is, as has been discussed above, conventionally designed with gold plating the electrical connection being provided by friction between the cylindrical surface of the connector 13 and the end portion 14 of the stud. A spring 27 is included in the connector in order to improve the connection between the end portion 14 of the stud and the PCB 10. The spring load necessitates that the connector 13 must be assembled and secured to the PCB 10 by screws (not shown).

The length of the whole male portion 12 can be around 11 mm or less, and the diameter of the mid-portion 16 can be between 3 to 4 mm. The female part of the snap assembly is consisting of the socket 18, formed as a recess in an upper cap portion 19 and by a base portion 20. The male head portion 15 may have a centered cavity 21 which is open at the terminal end of the male head portion. The cavity 21 is for fitting over a guiding stud 22 of a snap in accordance with the disclosure above. The guiding stud 22 may be an integral portion of the base portion 14. The base portion 20 can be made of a non-conductive material such as a plastic or rubber based material. The guiding stud can be rigid or it may have some, preferably a slight, degree of flexibility. The guiding stud 22 can take the geometry of a standard cylinder or, as shown, it can be advantageous for the guiding stud 22 to have a conical geometry. By having a conical geometry it allows for a stud 12 to have a slightly off alignment when entering the socket region and then aids in the centering and alignment of the stud 12 in to the detachably secured position as shown in FIG. 3.

The presence of a guiding stud 22 in the snap socket 18 allows an enhanced stability of the connection between the stud 12 and the socket 18, also allowing for a significantly more compact snap design. The cavity 21 may be centered on the terminal end of the male head portion 15, or the cavity may be off center. The depth of the cavity 21 can be between 0.5 to 1.5 mm. A non-conductive, preferably water-proof material 23 can be added on top of the snaps.

A conductive wire spring 24 is provided for holding the male 15 end of the device 9 in a releasable manner within the socket region 18 of the snap. Additionally, the conductive wire spring 24 make, or at least partially makes, the electrical connection between at least one electrode 25 in a garment or heart rate monitor belt 26 and the male end 15 of the telemetric device 9.

In FIGS. 4a-4f are shown the basic element of the present invention; a flexible cap that facilitates the assembly of electronic components. It is preferably made in one piece of a sheet of a conductive material, like metal. It can be designed in a variety of versions and embodiments within the scope of the present invention, here are only shown a few. Referring now to the embodiment shown in FIG. 4a, the cap 30a has a generally horizontal top surface 31a, three vertical side elements 33a formed between a first bend 32a and a second bend 34a of the sheet material. An anchor member 35a is formed at the second bend 34a in a direction outwards from the side elements 34a. Due to manufacturing and design considerations, number of the side elements 33a may vary between 2-6, for example, and also the number of bends between the parts may be of any number. The essential functionality of the inventive cap is provided by the top surface 31a joining all the side elements 33a together, the side elements 33a and, optionally, the anchor members 35a.

Figure 4A:
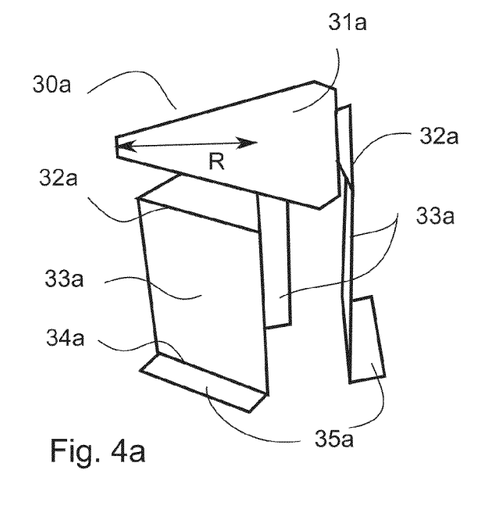
Figure 4B:
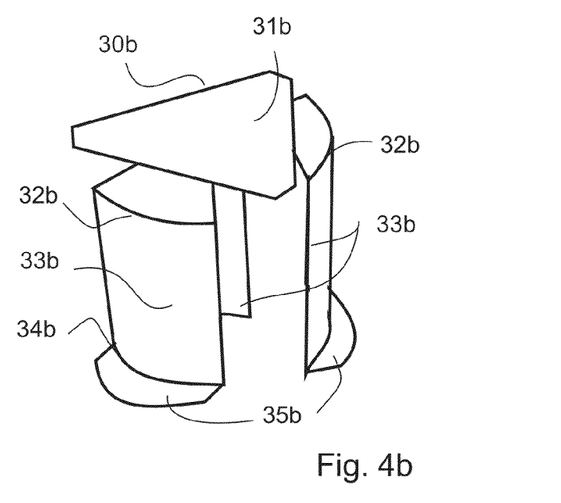

The embodiment shown in FIG. 4b shows a similar cap 30b, but with curved side elements 33b with bends 32b and 34b, and anchor members 35b. The remaining parts of the cap 30b are similar as the parts in FIG. 4a. With curved side elements, the insertion of the cap 30b in an aperture or hole 38A or 38B of a printed circuit board (PCB) 37 (see FIG. 5) requires less force than in the embodiment of FIG. 4a. When the cap 30a-30f is forced, as will be explained in the following, into an cylindrically shaped aperture with a radius corresponding to or only slightly greater than R, the side elements or members 33a-33f will deform more or less, depending on their shape, and bend to fit into the aperture. The side members 33a-33f will cut into the wall of the aperture and also become slightly deformed also in the part protruding through the aperture on the other side, thus locking the cap into place against any forces that would pull it out from the PCB.

The anchor members 35a and 35b will stop the movement of the cap as they engage with the edges of the aperture on the PCB side from where the caps are inserted, thus locking upon assembly the cap 30a or 30b to the PCB from both sides. The anchor members 35a, 35b also facilitates an assembly sequence that places and locks the caps 30a or 30b first in place into the printed circuit board apertures or holes 38A and 38B of FIG. 5, whereafter the end portion 14 of a male snap connector 41A can be inserted in to the already assembled cap.

Figure 4C:
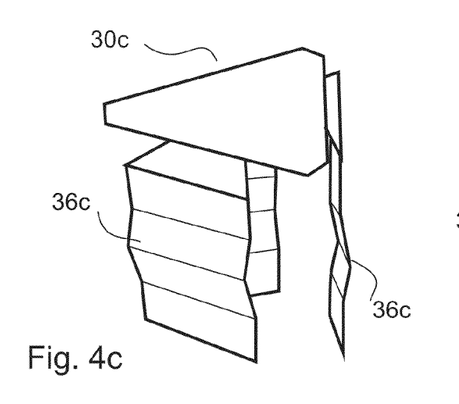
Figure 4D:
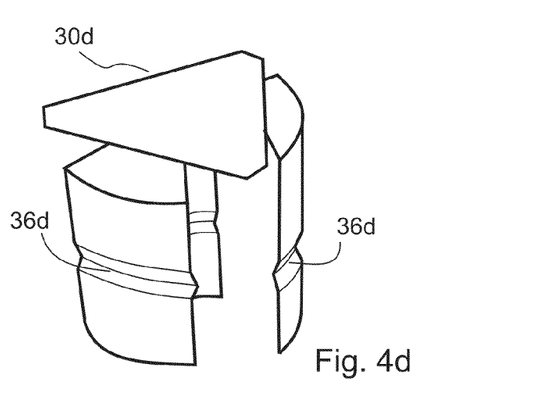

In FIGS. 4c and 4d are shown similar caps 30c and 30d as in FIGS. 4a and 4b, respectively, but without the anchor members. This is to reflect the fact that they are an option that may be beneficial in some embodiments of the invention, but not always essential to form the inventive and reliable electrical contact between a PCB and a snap connector. Here an embodiment is shown with an outwardly pointed middle bend 36c in FIG. 4c and an inwardly pointed bend 36d in FIG. 4d, respectively.

Figure 4E:
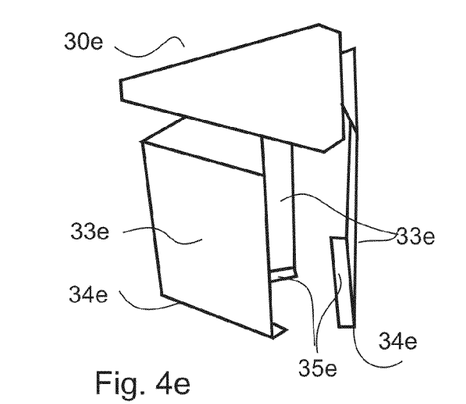
Figure 4F:
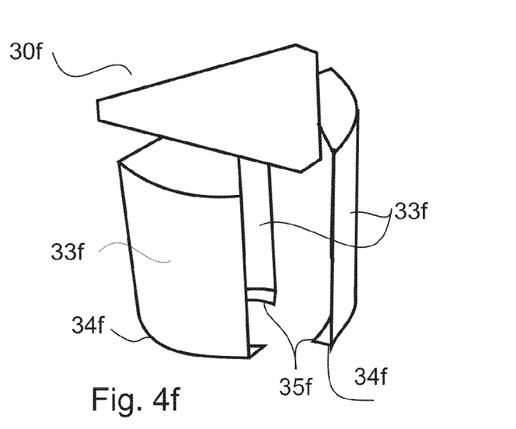

In FIGS. 4e and 4f are shown similar caps 30e and 30f as in FIGS. 4a and 4b, respectively, but with anchor members 35e and 35f turned inwards at the second bend 34e and 34f of the sheet material. Such anchor members will upon assembly cut into the snap end portion 14 and further secure the electrical connection between the cap and the male snap connector. However, as the side members 33e and 33f will upon assembly, due to these anchor members 35e or 35f slightly turn outwards as the snap end portion is inserted, they will also increase the deformation (see FIGS. 7a-c) of the side members and thus the friction between the cap and the PCB aperture. In this way both the locking function of the caps 30e, 30f and the electrical contact between them and the PCB is enhanced. Obviously, any combination of anchors, bends and their directions are possible and the subject of design choices for a specific device and situation. FIGS. 4a-4f merely shows examples of different shapes and features of the cap.

Figure 5:
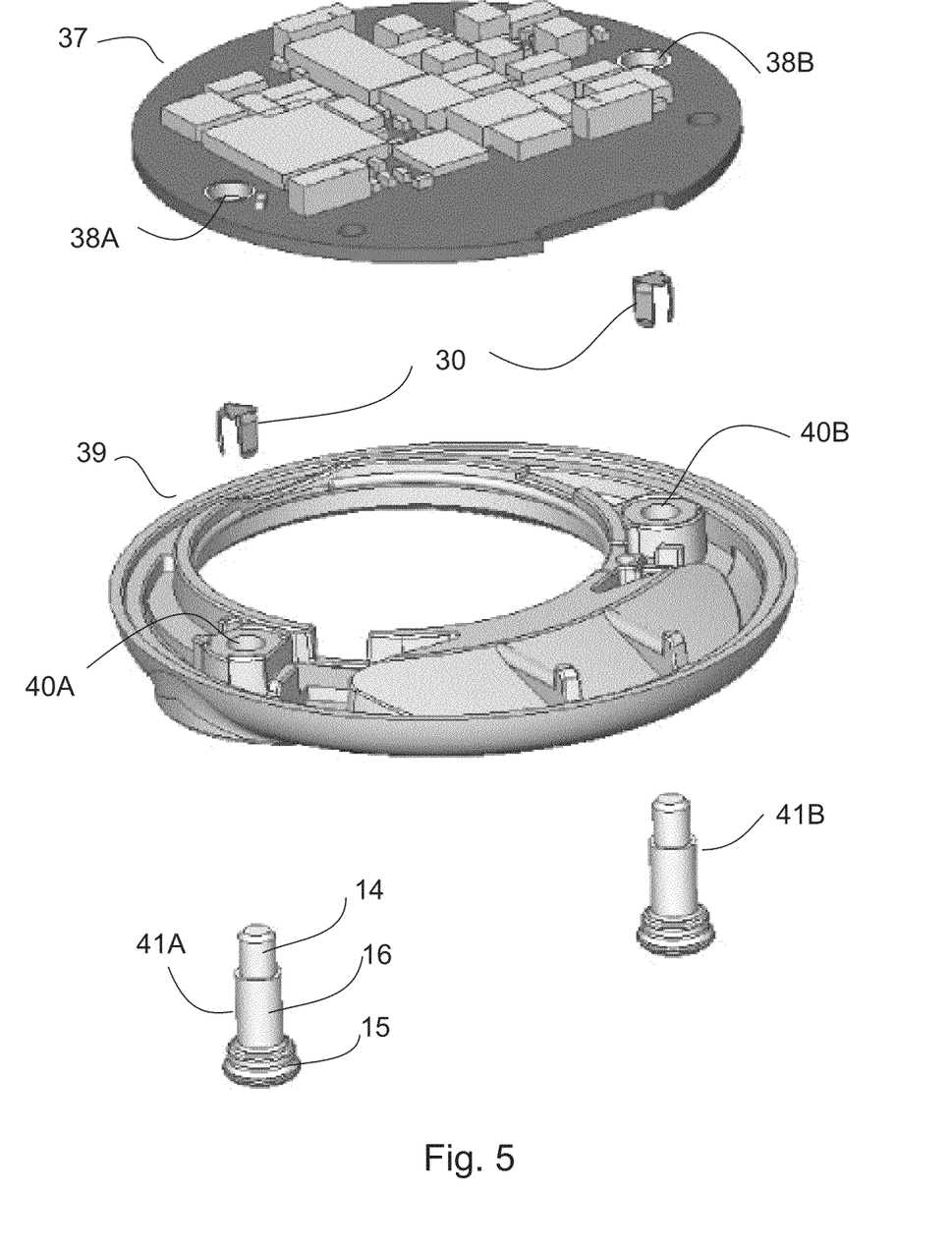
FIG. 5 shows an exploded assembly view of an electronic device making use of the present invention.

Referring now to FIG. 5, the cap 30 can for example be manufactured of a 0.15 mm thick stainless steel plate. It is preferably gold plated on the outside, to provide gold to gold contact against the printed circuit board apertures or holes 38A and 38B, which walls then are gold plated. On the inside, i.e. the side that comes against the end portion 14 of the stud 12, the contact surfaces may be steel against steel. Obviously, the cap can be manufactured of any metal or material providing proper electrical conductivity, flexibility and strength.

In FIG. 5 is shown the initial assembly setup of an electronic device making use of the present invention. The main elements of the device consists are a housing or body 39, a printed circuit board 37, a cover (not shown) closing the space over the PCB, and the connectors, i.e. the male snap connecting portions 41A and 41B.

As has been shown in FIG. 3, a the male snap connection portions 41A and 41B are elongate studs, with a male head portion 15 forming a first terminal end and an end portion 14 opposite said male head portion is forming a second terminal end. The studs are fastened to the housing 39 at the apertures 10A and 41B at the mid-portion 16 of the male snap connection portions 41A and 41B. This can be done by providing threads and by screwing the connection portions 41A and 41B into the apertures 40A and 40B. Alternatively, glue or ultrasound welding may be used. The corresponding apertures in the PCB 37 are marked as 38A and 38B, and the caps with reference number 30.

Figure 6:
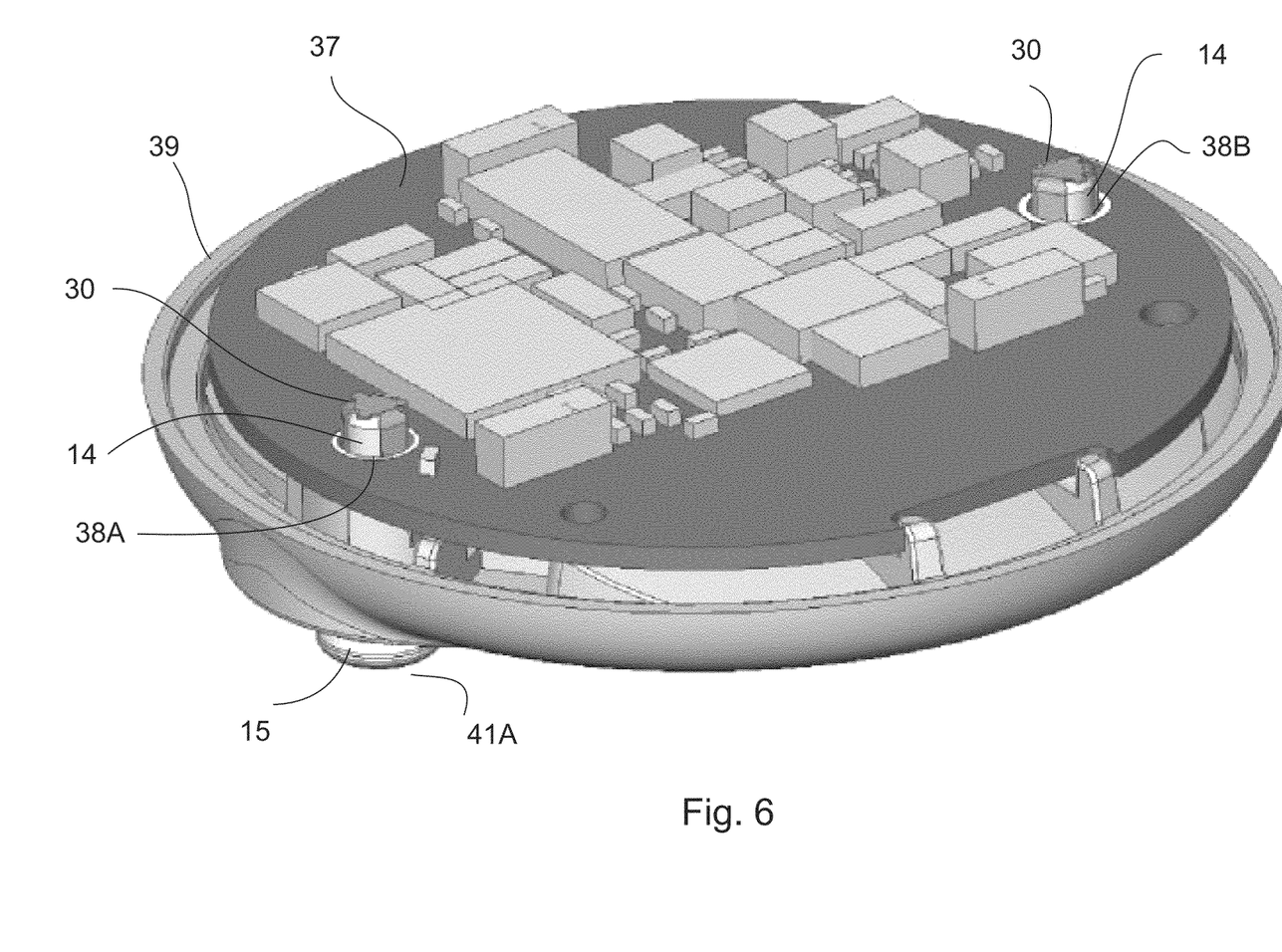
FIG. 6 shows a situation where the assembly of FIG. 5 is completed.

Referring now to FIG. 6, where the assembly of FIG. 5 is completed, it shows the printed circuit board 37 with the apertures or holes 38A and 38B being aligned to receive the second terminal ends 14 of the studs 41A and 41B (not visible) and their flexible caps 30.

The studs 41A and 41B have been inserted from underneath, first to the housing 39 (see FIG. 5) to firmly fix the mid-portion of the studs to the housing. Then the flexible caps 30 have been placed on the second terminal ends 14 of each stud 41A and 41B. After that, the assembly process continues by bringing the printed circuit board 37 and said housing 39 together, and by sliding the second terminals 14 and their flexible caps 30 into and through the apertures 38A and 38B underneath of the PCB. The anchor members 35 (see FIG. 4) of the caps 30 will stop the movement of the assemblies 14 and 30 through the apertures as they engage and make contact with the first side, or underneath side, of the printed circuit board. As shown in FIG. 6, the caps and the second terminal ends will form a protrusion at the second and opposite side of the printed circuit board 37.

The cap 30 cannot pass through the aperture 38A and 38B without being deformed. Due to the flexibility, shape and design of the caps 30, they will deform during the insertion in apertures 38A and 38B, and form an electrical connection and a mechanical lock between the portion 14 and the printed circuit board. The inner walls of the apertures 38A and 38B covered with a highly conductive material, preferably gold.

The anchor members 35 will stop the sliding movement and engage with the bottom side of the PCB 37, the side elements 33 will deform and cut into the walls of the apertures 38A and 38B, and finally, there will be some deformation of the side elements 33 also in the protruding part on the upper side of the PCB 37 in FIG. 6, effectively locking the end portions 14 of the studs and the PCB both mechanically and electrically in a very robust and secure electrical connection.

Figure 7A:
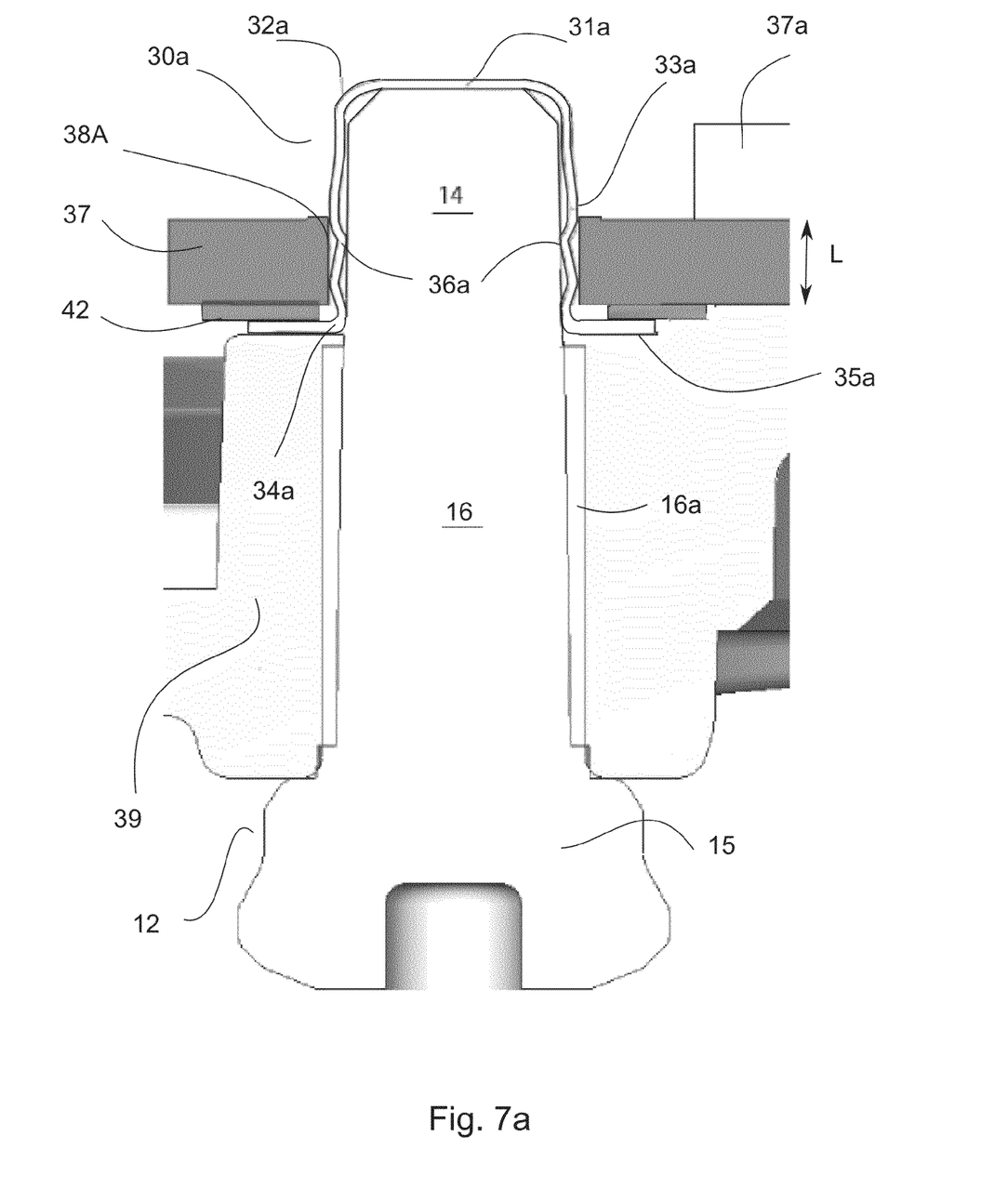

FIG. 7*a* shows an enlarged detail of one embodiment of the inventive assembly. In the center is seen a stud 12 with its male head portion 15, the opposite end portion 14 and the mid-portion 16, as has been described in FIG. 3. The mid-portion 16 has a threaded portion 16*a* which facilitates the fastening to the body 39 of the device by screwing. The end portion 14 of the stud has been covered by a cap 30*a* of FIG. 4*a*, and pushed through an aperture 38A of the printed circuit board 37. As can be seen, the deformations of the cap side elements 33*a* are considerable. It is of course ordinary design criteria to determine the correct diameter of the aperture 38A, its length L and the corresponding dimensions of the cap, in order to achieve a proper amount and kind of deformation.

The top surface 31*a* is preferably to be kept flat and pressed in the assembly against the end portion 14 in order to provide a secure steel-to-steel contact and eliminate movement of the stud inside the cap. The contact and the mechanical locking of the stud against the cap is enhanced by the deformation of the side elements 33*a*, that cut into the surface of the end portion with a spring force caused by the deformation. The same applies to the inside wall of the aperture 38A, that is preferably gold plated and connects to the circuitry 37*a* on top of the PCB 37 via conventional PCB wiring (not shown). The corresponding contact surface, i.e. the outside of the cap 30*a*, is preferably also gold plated. The upper and lower surface area of the PCB around the aperture may also be gold plated, as shown by layer 42. As can be seen, the compressed and deformed side elements 33*a* will extend outwards at the protrusion formed by the end portion 14 and the cap 30*a* on the upper or second side of the PCB 37. This deformation is reinforced by middle bends 36*a* (see FIG. 4), also adding friction between the cap and the aperture walls due to spring forces. Once the forces and deformation caused by the wall of the aperture 38A ends, the spring forces induced in the side elements 33*a* will make the side elements 33*a* to expand somewhat, thereby locking the cap in place against any downward movement in the aperture 38.

FIG. 7*a* also shows the function of the anchor members 35*a*, formed from the side elements by a second bend 34*a*, and effectively locking the cap 30*a* in place against any upward movement in the aperture 38. The anchor members 35*a* may advantageously have a somewhat more complicated structure that just a plain metal strip, e.g. corrugations or other flexible forms or bends allowing them to apply a spring force upwards toward the underside i.e. the first side of the PCB board 37 and the gold plating 42 as shown.

Figure 7B:
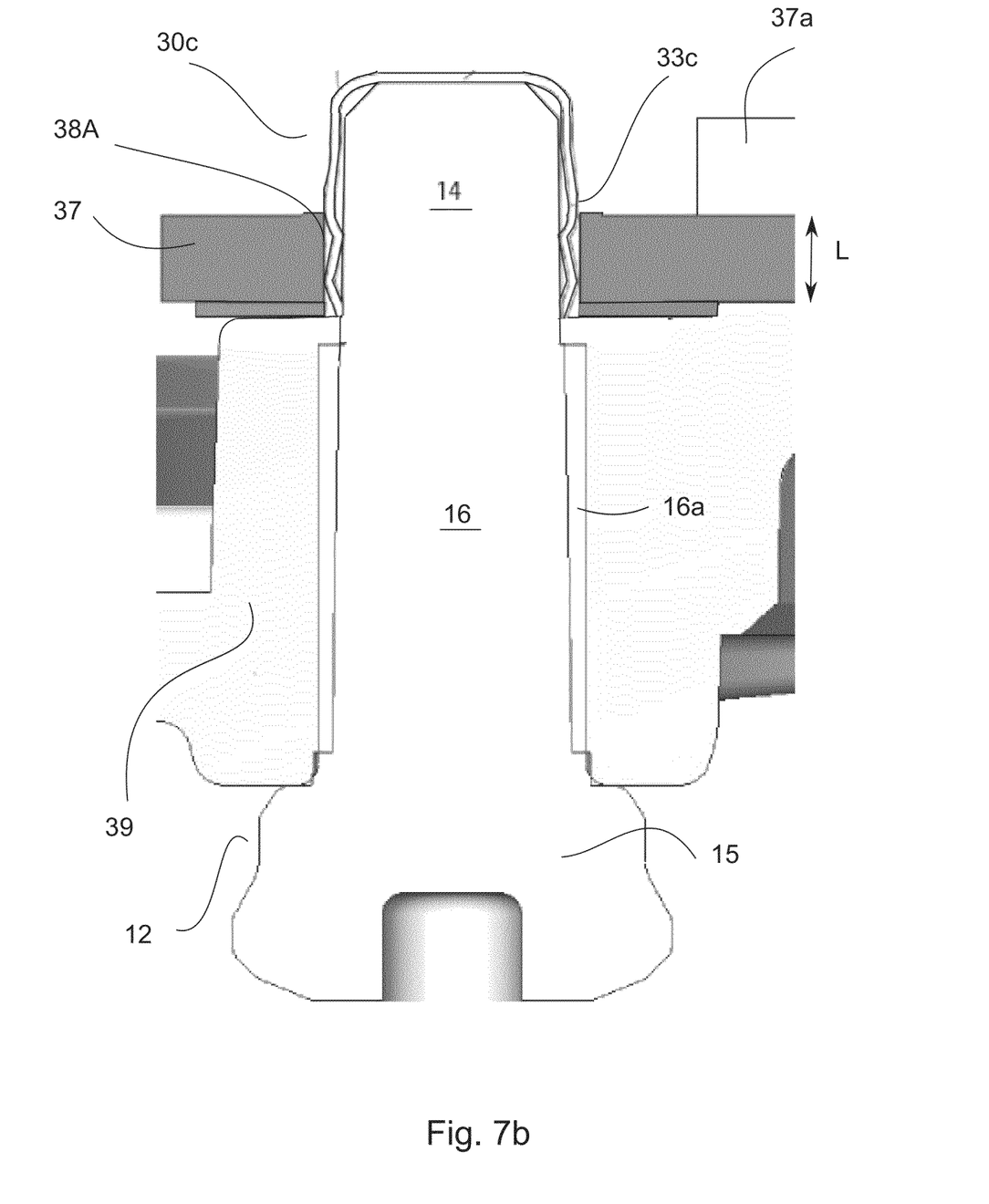

FIG. 7*b* shows an enlarged detail of another embodiment of the inventive assembly, where the cap 30*c* now correspond to the one shown in FIG. 4*c*. In all other respects the assembly is similar to the one in FIG. 7*a*, except that the anchor members 35*a* are not present in this embodiment. This means the assembly can safely only be made by first assembling the cap 30*c* on the end portion 14 and then bring it through the aperture 38. The anchoring function is now provided by the deformations of the side elements 33*c*.

Figure 7C:
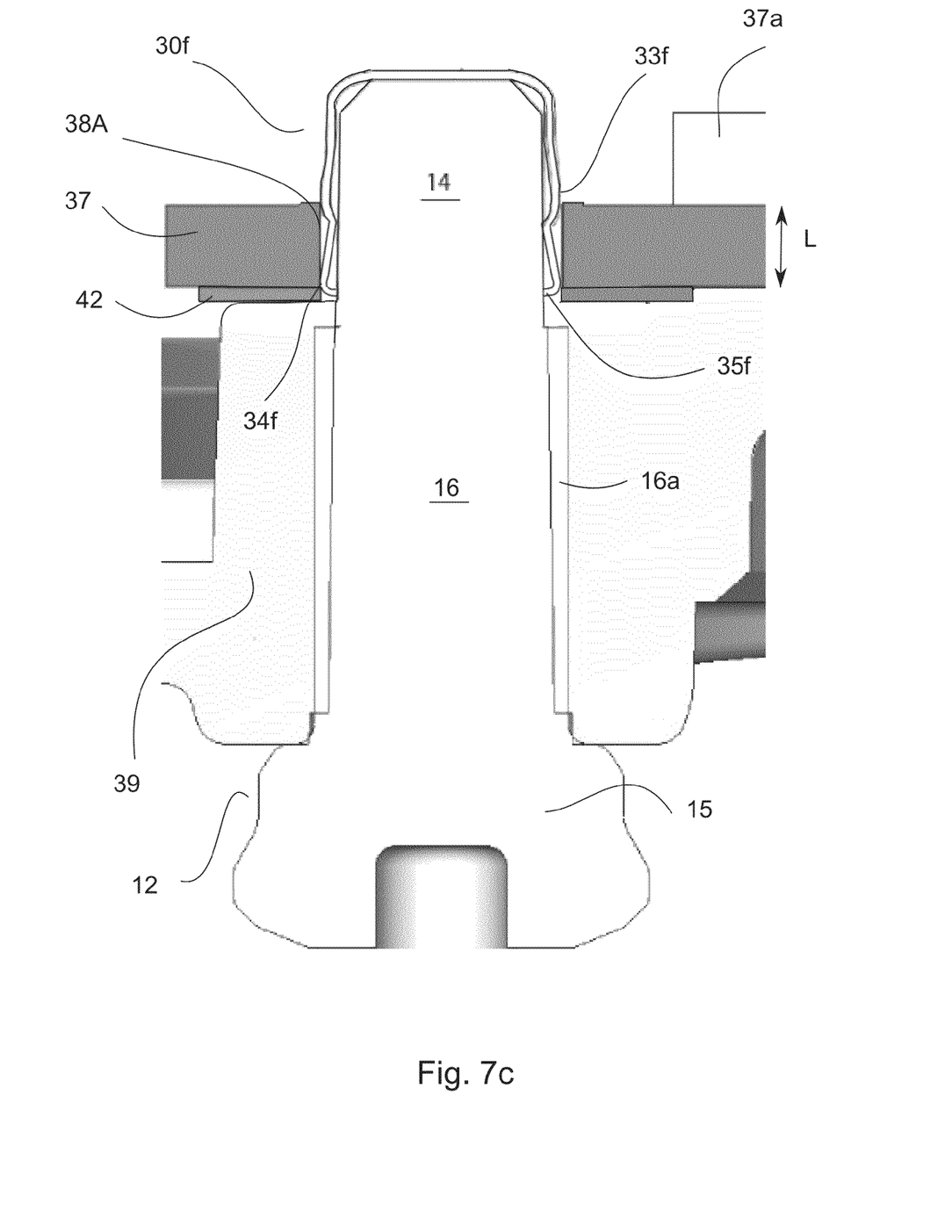

Finally, in FIG. 7*c* is shown an enlarged detail of another embodiment of the inventive assembly, where the cap 30*f* now correspond to the one shown in FIG. 4*f*. In all other respects the assembly is similar to the one in FIG. 7*a*, except that the anchor members 35*f* are turned inwards against and to engage with the end portion 14, as has been discussed in connection with FIGS. 4*e* and 4*f*.

As discussed herein, sports and health monitor devices often use a combination of electrodes and snaps in such an arrangement that they can be used to determine, measure and/or monitor various physiological signals of an individual or animal wearing a belt or garment with in-built electrodes. One of ordinary skill in the art will recognize countless electronic devices and telemetric devices which can be used within the scope of the present invention. Such electronic devices may or may not comprise a display and may or may not be capable of wirelessly transmitting information. Additionally, they may be capable of sending a wide variety of data not limited to heart rate to a remote receiver.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A mechanism for detachably connecting an electronic device to a female snap, the electronic device having a housing and a printed circuit board, the mechanism comprising:
   at least one male connection portion for providing a detachable connection of the electronic device to the female snap, the male connection portion comprising at least one elongate stud having:
      a male head portion capable of fitting within a socket region of the snap, the male head portion forming a first terminal end of the elongate stud,
      an end portion opposite the male head portion forming a second terminal end of the elongate stud and providing an electrical connection from the electronic device in the housing to the female snap,
      a mid-portion between the male head portion and the end portion at which the stud is fastened to the housing,
      the end portion extending through an aperture in the printed circuit board; and
   at least one flexible cap having a top surface and at least two side elements, the top surface configured to fit on the top of the second terminal end of the male connection portion, the end portion being adapted to engage the flexible cap, the cap being formed of a conductive sheet material, each of the side elements being formed as a leg joined to the top surface by a first bend of the sheet material, and the side elements being generally aligned with the sidewall of the end portion,
   whereby an electrical connection and a mechanical lock between the end portion and the printed circuit board are created by flexible deformation of the side members when the end portion extends through the aperture to engage the cap.

2. The mechanism of claim 1, wherein the at least two side elements of the flexible cap have an anchor member formed by a second bend opposite the first bend and in a transverse direction with respect to the direction of the side elements.

3. The mechanism of claim 2, wherein the anchor member formed by the second bend is directed outwards from the side elements to engage with the edge of the aperture of a first side of the printed circuit board.

4. The mechanism of claim 2, wherein the anchor member formed by the second bend is directed inwards from the side elements to engage with the sidewall of the end portion.

5. The mechanism of with claim 1, wherein the side element is formed as a plane.

6. The mechanism of claim 1, wherein the side element is curved with respect to the direction of the normal of the top surface.

7. The mechanism of claim 1, wherein the side elements of the flexible cap have a middle bend between the first and the second bend.

8. The mechanism of claim 1, wherein the device is a telemetric pulse transmitter to be attached to ECG electrodes in an electrode belt with a snap connection.

9. The mechanism of claim 1, wherein the device is a telemetric pulse transmitter to be attached to ECG electrodes integrated in a garment with a snap connection.

10. The mechanism of claim 1, wherein the device is an electromyography to be attached to EMG electrodes integrated in a garment with a snap connection.

11. A method for assembling components of an electronic device having a printed circuit board, a housing and at least one male snap connection portion for providing a detachable connection between the electronic device and a female snap, including the steps of:
   providing the at least one male connection portion as an elongate stud with a male head portion forming a first terminal end of the elongate stud, an end portion opposite the male head portion forming a second terminal end of the elongate stud, and a mid-portion between the male head portion and the end portion at which the stud is fastened to the a housing of said device,
   providing at least one flexible cap formed of a conductive sheet material, the cap having a top surface to fit on the top of the second terminal end of the elongate stud, at least two side elements each formed as a leg joined to the top surface by a first bend of the sheet material, the side elements being aligned along the wall of the end portion,
   providing the printed circuit board with at least one aperture aligned and adapted to receive the flexible cap and the second terminal end of the elongate stud;
   providing a the flexible cap in a position between the second terminal end of the elongate stud and the aperture of the printed circuit board;
   connecting the printed circuit board with the male connection portion and the cap by sliding the flexible cap and the second terminal end into the aperture of the printed circuit board to form an electrical connection and a mechanical lock between the end portion and the printed circuit board by flexible deformation of the side members.

12. A method for assembling components of an electronic device according to claim 11, wherein the flexible cap includes an anchor member formed by a second bend opposite the first bend in a general direction outwards with respect to the direction of the side elements, whereby the flexible cap is inserted into the aperture first whereafter the second terminal end is slid into the flexible cap to form the connection between the printed circuit board and the male connection portion.

13. A method for assembling components of an electronic device according to claim 11, wherein the flexible cap is first slid onto the second terminal end, whereafter the second terminal end is slid into the aperture to form the connection between the printed circuit board and the male connection portion.

14. A flexible cap for facilitating assembly of an electronic component of an electronic device, the component having at least one elongated stud-like connecting member with a first male snap connection portion providing a detachable connection between the first male snap connection portion and a female snap, and a second and opposite end portion forming a second terminal end of the stud connecting member and providing an electrical connection between the electronic device and the female snap, the cap being made of a conductive sheet material and having a generally horizontal top surface extending over the second end portion of the component, at least two generally vertical side elements each of which is formed as a leg joined to the top surface by a first bend of the sheet material, whereby the cap is adapted to create an electrical connection and a mechanical lock between the electronic component and an aperture of a printed circuit board of the electronic device by flexible deformation of the side members when the connecting member is slid into the cap and passed through the aperture of the printed circuit board.

15. A flexible cap according to claim 14, wherein the side elements of the flexible cap have an anchor member formed by a second bend opposite the first bend of the side elements and in a transverse direction with respect to the direction of the side elements.

16. A flexible cap according to claim 15, wherein the anchor member is directed outwards from the side elements to engage with the edge of the aperture on the side of its insertion direction of the printed circuit board.

17. A flexible cap according to claim 15, wherein the anchor is directed inwards from the side elements to engage with the wall of the end portion.

18. A flexible cap according to claim 14, wherein the surface of the side element is formed as a plane.

19. A flexible cap according to claim 14, wherein the surface of the side element is curved with respect to the direction of the normal of the top surface.

20. A flexible cap according to claim 14, wherein the side elements of said flexible cap have a middle bend between the first and the second bend.

21. A flexible cap according to claim 14, wherein the cap is made out of one piece of a stainless steel sheet and comprises three side elements.

* * * * *